(12) United States Patent
Ci

(10) Patent No.: US 10,773,125 B2
(45) Date of Patent: Sep. 15, 2020

(54) MULTI-ANGLE ELECTRIC EXERCISE INSTRUMENT AND CONTROL METHOD

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 113 days.

(21) Appl. No.: 15/954,370

(22) Filed: Apr. 16, 2018

(65) Prior Publication Data

US 2019/0314683 A1 Oct. 17, 2019

(51) Int. Cl.
*A63B 24/00* (2006.01)
*A61B 5/0205* (2006.01)
(Continued)

(52) U.S. Cl.
CPC ........ *A63B 24/0087* (2013.01); *A61B 5/0022* (2013.01); *A61B 5/02055* (2013.01); *A61B 5/0402* (2013.01); *A61B 5/4803* (2013.01); *A61M 21/02* (2013.01); *A63B 21/4034* (2015.10); *A63B 21/4035* (2015.10); *A63B 24/0062* (2013.01); *G05B 15/02* (2013.01); *A61B 5/01* (2013.01); *A61B 5/053* (2013.01); *A61M 2021/0027* (2013.01); *A61M 2205/80* (2013.01); *A63B 2023/006* (2013.01); *A63B 2024/0093* (2013.01);
(Continued)

(58) Field of Classification Search
CPC ........ A63B 2024/0096; A63B 24/0087; A63B 21/4013-4017; A63B 23/08; A63B 23/085; A63B 2026/006; A63B 26/003; A63B 2230/655; A63B 2230/045; A63B 2024/0093; A63B 21/4034; A63B 21/4035; A63B 24/0062; A61L 35/02055; A61L 35/0402; A61L 35/4803; A61L 35/0022; A61L 35/01; A61M 2021/0027; A61M 21/02; A61M 2205/80; G05B 15/02; A61B 5/02055; A61B 5/0402; A61B 5/4803; A61B 21/4034; A61B 5/0022; A61B 5/01; A61B 5/053; A61B 5/00

See application file for complete search history.

(56) References Cited

U.S. PATENT DOCUMENTS

| | | | | |
|---|---|---|---|---|
| 3,711,812 A | * | 1/1973 | Cherry | A63B 22/02 338/200 |
| 5,632,711 A | * | 5/1997 | Hwang | A63B 22/14 482/146 |

(Continued)

*Primary Examiner* — Nyca T Nguyen
(74) *Attorney, Agent, or Firm* — Cantor Colburn LLP

(57) ABSTRACT

The present disclosure discloses a multi-angle electric exercise equipment, including: a meridian stretching standing plate which includes a base, standing plate handrails, and an angle adjusting standing plate, a health management system which comprises a health inspection and control unit and a health analysis unit; the standing plate handrails are provided on the base; the angle adjusting standing plate is provided facing the handrails and at one side of the base; an upper surface of the angle adjusting standing plate is provided with a treading area, the angle adjusting standing plate is adjustable in angle; the health analysis unit is used to analyze health information collected by the health inspection and control unit, acquire a health analysis result, and provides a health solution. The present disclosure is mainly used for stretching of meridians of human body, providing multi-angle stretching angle adjustment for exercises of stepped difficulty.

15 Claims, 2 Drawing Sheets

(51) Int. Cl.
*A61B 5/0402* (2006.01)
*A61B 5/00* (2006.01)
*A63B 21/00* (2006.01)
*G05B 15/02* (2006.01)
*A61B 5/01* (2006.01)
*A61B 5/053* (2006.01)
*A63B 23/00* (2006.01)
*A61M 21/00* (2006.01)
*A61M 21/02* (2006.01)

(52) U.S. Cl.
CPC ..... *A63B 2225/096* (2013.01); *A63B 2225/52* (2013.01); *A63B 2230/045* (2013.01); *A63B 2230/505* (2013.01); *A63B 2230/655* (2013.01)

(56) References Cited

U.S. PATENT DOCUMENTS

| | | | | |
|---|---|---|---|---|
| 5,833,577 | A * | 11/1998 | Hurt | A63B 22/02 482/54 |
| 5,921,899 | A * | 7/1999 | Rose | A63B 5/11 482/112 |
| 5,944,635 | A * | 8/1999 | Butler, Jr. | A63B 22/02 482/54 |
| 6,087,792 | A * | 7/2000 | Wang | A63B 22/02 318/362 |
| 6,225,977 | B1 * | 5/2001 | Li | G05G 1/52 345/156 |
| 6,676,579 | B1 * | 1/2004 | Lin | A63B 22/0012 482/146 |
| 6,692,419 | B2 * | 2/2004 | Chen | A63B 22/18 482/146 |
| D522,074 | S * | 5/2006 | Dummel | D21/662 |
| 7,074,167 | B1 * | 7/2006 | Chen | A61H 7/001 482/146 |
| 7,278,976 | B1 * | 10/2007 | Chen | A61H 1/005 601/30 |
| 7,374,522 | B2 * | 5/2008 | Arnold | A63B 21/005 482/146 |
| 7,666,121 | B2 * | 2/2010 | Zhou | A63B 21/154 482/146 |
| 9,393,458 | B1 * | 7/2016 | LaCaze | A63B 21/22 |
| 9,731,163 | B2 * | 8/2017 | Henson | A63B 22/18 |
| 9,782,625 | B1 * | 10/2017 | Blum | A63B 24/0087 |
| 2002/0016235 | A1 * | 2/2002 | Ashby | A63B 21/005 482/8 |
| 2003/0064862 | A1 * | 4/2003 | Hald | A63B 22/0023 482/51 |
| 2003/0199374 | A1 * | 10/2003 | Perry | A61H 1/005 482/146 |
| 2004/0014566 | A1 * | 1/2004 | Kao | A63B 24/00 482/8 |
| 2004/0018918 | A1 * | 1/2004 | Reyes | A63B 22/02 482/54 |
| 2005/0113681 | A1 * | 5/2005 | DeFreitas | A61B 6/502 600/426 |
| 2005/0209061 | A1 * | 9/2005 | Crawford | A63B 22/0056 482/54 |
| 2006/0217243 | A1 * | 9/2006 | Feldman | A63B 21/002 482/91 |
| 2006/0258289 | A1 * | 11/2006 | Dua | H04M 1/7253 455/41.3 |
| 2007/0184953 | A1 * | 8/2007 | Luberski | A63B 22/18 482/146 |
| 2007/0207900 | A1 * | 9/2007 | Huang | A63B 26/003 482/51 |
| 2007/0213179 | A1 * | 9/2007 | Trandafir | A61H 1/005 482/51 |
| 2007/0239088 | A1 * | 10/2007 | Wu | A61H 1/005 601/49 |
| 2007/0290632 | A1 * | 12/2007 | Stevens | A61H 1/003 318/135 |
| 2008/0242511 | A1 * | 10/2008 | Munoz | A63B 22/02 482/5 |
| 2008/0280740 | A1 * | 11/2008 | Knecht | A61B 3/113 482/146 |
| 2008/0300520 | A1 * | 12/2008 | Shin | A61H 1/003 601/49 |
| 2009/0069157 | A1 * | 3/2009 | Wilhelm | A61H 1/003 482/51 |
| 2009/0227426 | A1 * | 9/2009 | Dubar | A63B 21/0004 482/34 |
| 2010/0087302 | A1 * | 4/2010 | Fukunaga | A61H 1/005 482/146 |
| 2010/0167887 | A1 * | 7/2010 | Berry | A63B 22/18 482/147 |
| 2011/0039669 | A1 * | 2/2011 | Stewart | A63B 21/015 482/146 |
| 2011/0256983 | A1 * | 10/2011 | Malack | A61H 1/0266 482/4 |
| 2011/0294625 | A1 * | 12/2011 | Flake | A63B 22/0264 482/54 |
| 2012/0041767 | A1 * | 2/2012 | Hoffman | A63B 24/0059 705/1.1 |
| 2012/0238921 | A1 * | 9/2012 | Kuehne | A61H 1/0229 601/5 |
| 2012/0264569 | A1 * | 10/2012 | Escobedo | A63B 22/0023 482/5 |
| 2013/0083941 | A1 * | 4/2013 | Rogel | H04R 1/02 381/86 |
| 2013/0274065 | A1 * | 10/2013 | Ashby | A63B 24/00 482/4 |
| 2013/0274069 | A1 * | 10/2013 | Watterson | A63B 24/0087 482/9 |
| 2013/0316827 | A1 * | 11/2013 | Kang | A63B 22/02 463/36 |
| 2014/0038777 | A1 * | 2/2014 | Bird | A63B 21/0058 482/5 |
| 2015/0173652 | A1 * | 6/2015 | Brunner | A61B 5/112 482/7 |
| 2015/0182791 | A1 * | 7/2015 | Tsuzuki | A63B 21/023 482/139 |
| 2015/0251049 | A1 * | 9/2015 | Kolvenbach | A63B 21/00076 482/6 |
| 2015/0262459 | A1 * | 9/2015 | Munro | G08B 5/38 340/522 |
| 2015/0328497 | A1 * | 11/2015 | Doucot | A63B 23/08 482/146 |
| 2016/0107025 | A1 * | 4/2016 | Chang | A61H 1/0266 482/131 |
| 2016/0144236 | A1 * | 5/2016 | Ko | A63B 24/0062 434/247 |
| 2016/0175643 | A1 * | 6/2016 | Kueker | A63B 24/0087 482/5 |
| 2016/0193497 | A1 * | 7/2016 | Arst | A63B 22/0292 482/5 |
| 2016/0256737 | A1 * | 9/2016 | Yoshioka | A63B 23/0405 |
| 2017/0337033 | A1 * | 11/2017 | Duyan | G06F 3/165 |
| 2018/0133583 | A1 * | 5/2018 | Tran | A63B 69/38 |
| 2018/0237148 | A1 * | 8/2018 | Hehn | B64C 39/024 |
| 2018/0296157 | A1 * | 10/2018 | Bleich | A61B 5/486 |
| 2018/0326286 | A1 * | 11/2018 | Rathi | A63B 71/0622 |

* cited by examiner

MULTI-ANGLE ELECTRIC EXERCISE INSTRUMENT AND CONTROL METHOD

TECHNICAL FIELD

The present disclosure relates to the field of exercise and fitness equipment, and particularly to a multi-angle electric exercise equipment and a control method.

BACKGROUND

In recent years, with the concentration of urban population and the accelerated pace of life, the population in sub-health is increasing significantly. Meanwhile, with the improvement of both consumption power and concept, people pay more attention to taking care of their own health, thus many types of household exercise and fitness equipment emerged.

The existing household exercise and fitness equipment is mainly classified into two types by function: one type is exercise equipment, such as massage chair and treadmill; the other type is measurement equipment, such as thermometer and glucometer. Up to now, there is still a gap in the market of developing fitness equipment for meridian stretching exercise with personalized and suitable angles and further regulating the meridians of the whole body in the aspect of combining the intelligentized health management with theories of the traditional Chinese medicine meridian and exercise for preserving health, which has a wide-ranging research space and market prospect.

SUMMARY

An object of the present disclosure is to provide a multi-angle electric exercise equipment and control method which make users capable of performing meridian fitness to overcome the problems existing in the prior art.

In order to achieve the above object, the present disclosure provides a multi-angle electric exercise equipment. The multi-angle electric exercise equipment comprises a meridian stretching standing plate and a health management system, wherein the meridian stretching standing plate comprises a base, standing plate handrails, and an angle adjusting standing plate; the health management system comprises a health inspection and control unit and a health analysis unit; the health analysis unit is provided by local or cloud service, and linked with the health inspection and control unit in communication; the standing plate handrails are provided on the base; the angle adjusting standing plate is provided facing the handrails and at one side of the base; an upper surface of the angle adjusting standing plate is provided with a treading area, the angle of the angle adjusting standing plate is adjustable with one side edge as a baseline; the health analysis unit is used to analyze health information of a user collected by the health inspection and control unit, acquire a health analysis result of the user, and provide a health solution.

Furthermore, as described above, with respect to the multi-angle electric meridian exercise equipment, the angle adjusting standing plate comprises a seat, an outer case and a lifting mechanism; the outer case covers over the seat; the lifting mechanism is provided inside the seat and the outer case; an upper surface of the outer case is provided with a treading area; the lifting mechanism enables the angle of the outer case to be adjusted with one side edge as a baseline.

Furthermore, as described above, with respect to the multi-angle electric meridian exercise equipment, a slide track which is foldable on the base is provided between the base and the angle adjusting standing plate, and the angle adjusting standing plate rests on the slide track in a manner of being able to slide back and forth.

Furthermore, as described above, with respect to the multi-angle electric meridian exercise equipment, the treading area is provided with an anti-slip mat therein.

Furthermore, as described above, with respect to the multi-angle electric meridian exercise instrument, the health inspection and control unit further comprises a display module, a central control module, a data processing module, a physical sign inspection module and a wireless transmission module; the central control module is provided in a middle part of the handrails, and is electrically connected to the display module, the data processing module and the wireless transmission module; the data processing module is electrically connected to the physical sign inspection module, for converting an analog signal detected by the physical sign inspection module to a digital signal; the display module is used to select a health inspection item and display health information and a health solution.

Furthermore, as described above, with respect to the multi-angle electric meridian exercise equipment, the physical sign inspection module comprises foot induction contacts, electrocardio detecting contacts, and a body temperature detecting contact.

Furthermore, as described above, with respect to the multi-angle electric meridian exercise equipment, the health inspection and control unit also comprises a music modulation module; the music modulation module is used to collect user's voice information and acquire a basic frequency of a user voice; the central control module determines a voice basic frequency interval of the user according to the basic frequency of the voice, and selects and plays music matched with the voice basic frequency interval.

Furthermore, as described above, with respect to the multi-angle electric meridian exercise equipment, the health inspection and control unit is further integrated with a soft start power button, an earphone interface, an up button, and a down button; the soft start power button is provided below the display module, and the up button and the down button are used to control the angle adjustment of the angle adjusting standing plate; the earphone interface is provided below the display module.

Furthermore, as described above, the multi-angle electric meridian exercise instrument also comprises a power management unit and a hot start power switch, the power management unit being used for power-off protection and charge/discharge management, and the hot start power switch is provided on the base.

The present disclosure further provides a control method of the multi-angle electric exercise equipment, including:

S1: performing angle adjustment of the angle adjusting standing plate and selection of the health inspection item through the health inspection and control unit;

S2: performing, by the angle adjusting standing plate, the angle adjustment of the angle adjusting standing plate as needed; after performing the selection of the health inspection item, collecting and monitoring health information of a user according to the selected health inspection item;

S3: processing the health information of the user, and acquiring the health analysis result of the user;

S4: providing a corresponding modulating method and the exercise equipment according to physical condition information of the user.

In the above technical solutions, on the basis of the traditional Chinese medicine theory, the present disclosure provides the stretching standing plate capable of being tilted by multiple angles. When the user stands on the stretching standing plate, owing to the reasonable angle adjustment of the above angle adjusting standing plate, the user can perform meridian stretching movements on this standing plate, thus providing a type of brand-new health maintenance exercise equipment. The present disclosure is simple in structure and relatively low in cost, and since it is reasonably provided on the basis of the traditional Chinese medicine theory, it has excellent exercise and maintenance effects, and is adapted to functional requirements of modern people to their own health maintenance. Moreover, through the health management system, the traditional Chinese medicine music therapy can be specifically performed according to the detection condition of the user and a corresponding health management solution can be provided.

BRIEF DESCRIPTION OF THE DRAWINGS

In order to illustrate the technical solutions of embodiments of the present disclosure or the prior art more clearly, the accompanying drawings which need to be used in the description of the embodiments will be briefly described below. Apparently, the accompanying drawings described in the following are merely for some embodiments of the present disclosure, and a general person skilled in the art still can obtain other accompanying drawings according to these accompanying drawings.

DETAILED DESCRIPTION OF THE EMBODIMENTS

In order to enable a person skilled in the art to better understand the technical solutions of the present disclosure, the present disclosure will be further described in detail below with reference to the accompanying drawings.

Figure 1:
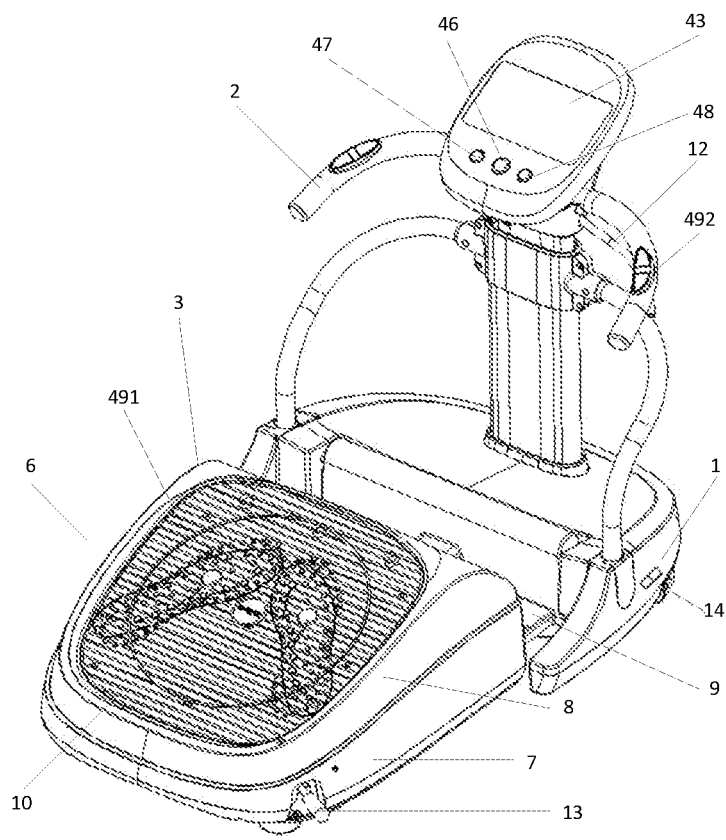
FIG. 1 is a front view of a multi-angle electric exercise equipment of an embodiment of the present disclosure.
Figure 2:
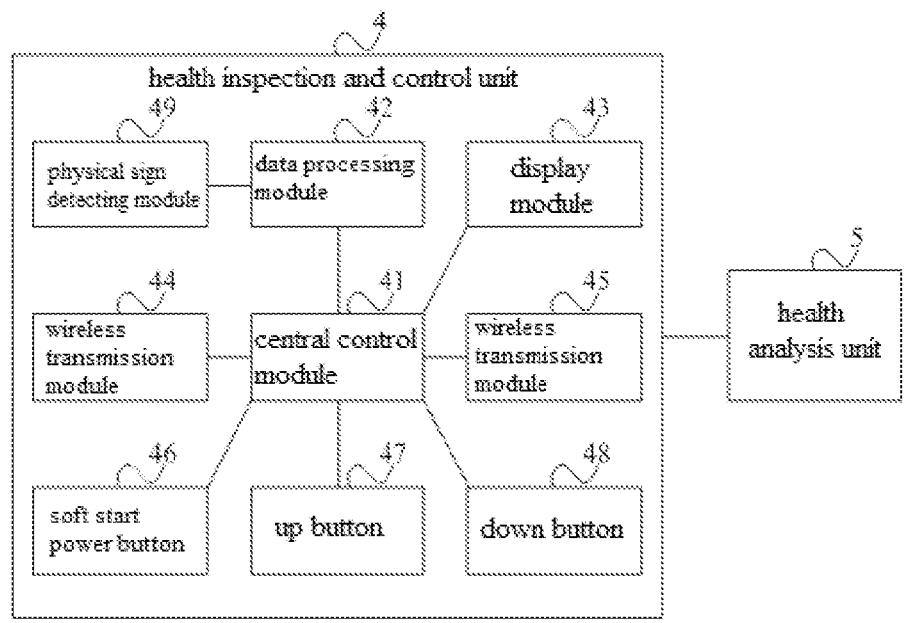
FIG. 2 is a schematic view of an electronic function module of the multi-angle electric exercise instrument of an embodiment of the present disclosure.

As shown in FIG. 1 and FIG. 2, the present disclosure provides a multi-angle electric exercise equipment, including a meridian stretching standing plate and a health management system. Wherein the meridian stretching standing plate comprises a base 1, standing plate handrails 2 and an angle adjusting standing plate 3; wherein the health management system includes a health inspection and control unit 4 and a health analysis unit 5; the health analysis unit is provided by local or cloud service, and is linked with the health inspection and control unit in communication; the standing plate handrails are provided on the base, and preferably, the standing plate handrails can be in lifting connection with the base, and can be adjusted through a handrail lifting adjustment lever 12 provided below the standing plate handrails; the angle adjusting standing plate is provided facing the handrails and at one side of the base; an upper surface of the angle adjusting standing plate is provided with a treading area 6, the angle of the angle adjusting standing plate 3 can be adjusted with one side edge as a baseline, preferably, a tilt angle is 0°~45°; the health analysis unit is used to analyze health information of a user collected by the health inspection and control unit, acquire a health analysis result of the user, and provide a health solution. By implementing the above technical solution, the angle adjusting standing plate 3 capable of being tilted by multiple angles of 0°~45° is provided on the basis of the traditional Chinese medicine theory. When the user stands on the stretching standing plate, owing to the reasonable angle adjustment of the above angle adjusting standing plate 3, the user can perform meridian stretching movements on this standing plate, thus providing a type of brand-new health maintenance exercise equipment. Since the user exercises on the inclined angle adjusting standing plate 3, a beginner is possibly not be able to stand firm due to unbalanced center of gravity, the handrails are provided right in front of the angle adjusting standing plate 3, further improving the security of exercise, and the handrails further is telescopic and adjustable up and down, and further can satisfy requirements of users of different heights. The present disclosure is simple in structure and relatively low in cost, and since it is reasonably provided on the basis of the traditional Chinese medicine theory, it has excellent exercise and maintenance effects, and is adapted to functional requirements of modern people to their own health maintenance.

Furthermore, as described above, with respect to the multi-angle electric exercise equipment, the angle adjusting standing plate 3 comprises a seat 7, an outer case 8, and a lifting mechanism (not shown in the figures); the outer case covers over the seat; the lifting mechanism is provided between the seat 7 and the outer case 8 at one side close to the handrails 2; an upper surface of the outer case 8 is provided with a treading area; the lifting mechanism enables the outer case to be adjusted in angle with one side edge as a baseline, specifically, adjustable gears are gear two or higher. The stretching standing plate with such a structure has relatively high security, and its outer case 8 covering over the seat 7 can perfectly shield the lifting mechanism therein so as to avoid occurrence of phenomena such as pinching and scratching. Moreover, since the outer case has relatively high plasticity, different external designs can be made thereto, thus improving the aesthetics of the appearance of the present product, and enabling it to be more easily integrated into the household environment.

In some embodiments, a slide track 9 being foldable on the base is provided between the base and the angle adjusting standing plate 3, and the angle adjusting standing plate 3 can rest on the slide track in a manner of sliding back and forth. Such a structure not only can transversely adjust a position of the angle adjusting standing plate 3 to further satisfy requirements of users with different body types. Moreover, the angle adjusting standing plate can be folded on the base through the slide track to further save space. Preferably, a standing plate telescopic adjustment lever 13 is further included, and by adjusting the standing plate telescopic adjustment lever, the distance between the angle adjusting standing plate and the base 1 can be adjusted. This provision can be adapted to users of different heights. Since lengths of arms are also different when the heights are different, a horizontal distance between the angle adjusting standing plate and the standing plate handrails provided on the base 1 also should be adjusted adaptively.

In some embodiments, the treading area is provided with an anti-slip mat 10 therein. Thus, the technical problem of slip resistance in the treading area due to inclination of the angle adjusting standing plate 3 is well solved. Moreover, induction contacts can be further provided to be not covered by the anti-slip mat in the treading area and on positions where two feet rest. When the user stands on the angle adjusting standing plate 3, the induction contacts will send a non-angle adjustment signal, so as to control the angle adjusting standing plate 3 to be fixed in a certain angle state, thus ensuring that the user completes the stretching movements successfully.

In some embodiments, as described above, with respect to the multi-angle electric exercise equipment, the health inspection and control unit further includes a display module 43, a central control module 41, a data processing module 42, a physical sign inspection module 49, and a wireless transmission module 44; the central control module 41 is provided in a middle part of the handrails, and is electrically connected to the display module, the data processing module and the wireless transmission module; the data processing module 42 is electrically connected to the physical sign detecting module 49, for converting an analog signal detected by the physical sign inspection module to a digital signal; the display module 43 is used to select a health inspection item and display health information and a health solution.

In some embodiments, the physical sign inspection module 49 includes: foot induction contacts 491, electrocardio detecting contacts 492, and a body temperature detecting contact (not shown in the figures).

Furthermore, as described above, with respect to the multi-angle electric exercise instrument the health inspection and control unit further includes a music modulation module 45; the music modulation module 45 is used to collect user's voice information and acquire a basic frequency of a user voice. The central control module 41 determines a voice basic frequency interval of the user according to the basic frequency of the voice, and selects and plays music matched with the voice basic frequency interval. Preferably, the music modulation module 45 includes a voice recognizing module and a power amplifying module; the voice recognizing module is used to collect the user's voice information; the power amplifying module is used to play the music; and the voice recognizing module and the power amplifying module are both provided in positions around the display module 43 and facing the angle adjusting standing plate 3.

In some embodiments, as described above, with respect to the multi-angle electric exercise equipment, the health inspection and control unit is further integrated with a soft start power button 46, an earphone interface (not shown in the figures), an up button 47, and a down button 48; the soft start power button 46 is provided below the display module 43, and the up button 47 and the down button 48 are used to control the angle adjustment of the angle adjusting standing plate; the earphone interface is provided above the display module. The soft start power button 46 is used to switch off the equipment through a software system.

In some embodiments, a power management unit and a hot start power switch 14 are further included. The power management unit is used for power-off protection and charge/discharge management, and the hot start power switch 14 is provided on the base 1. The power management unit further provides a circuit protect module for power-off protection and charge/discharge management. The hot start power switch 14 is connected to a main power for shutting off all the power of the equipment.

Figure 3:
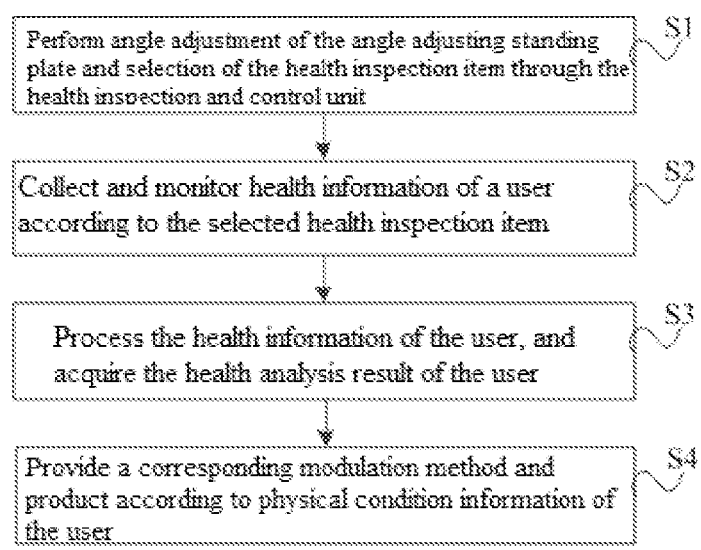
FIG. 3 is a schematic flow chart of a control method for the multi-angle electric exercise instrument of an embodiment of the present disclosure.

As shown in FIG. 3, the present disclosure further provides a control method for the above multi-angle electric exercise equipment, including:

S1: performing angle adjustment of the angle adjusting standing plate 3 and selection of the health inspection item through the health inspection and control unit 4;

S2: performing, by the angle adjusting standing plate 3, performing the angle adjustment of the angle adjusting standing plate 3 as needed; after performing the selection of the health inspection item, collecting and monitoring health information of a user according to the selected health inspection item;

S3: processing the health information of the user, and acquiring the health analysis result of the user;

S4: providing a corresponding modulation method and product according to physical condition information of the user.

The above merely describes some exemplary embodiments of the present invention in an illustrative manner. It goes without saying that a person ordinarily skilled in the art can modify the embodiments described through various different manners without departing from the spirit and scope of the present invention. Therefore, the above accompanying drawings and description are essentially illustrative, and should not be construed as limitation to the scope protected by the claims of the present invention.

What is claimed is:

1. A multi-angle electric exercise equipment, comprising a meridian stretching standing plate and a health management system, wherein the meridian stretching standing plate comprises a base, standing plate handrails, and an angle adjusting standing plate; the health management system comprises a health inspection and control unit and a health analysis unit; the health inspection and control unit further comprises a display module, a central control module, a data processing module, a physical sign inspection module, and a wireless transmission module; the physical sign inspection module comprises: foot induction contacts, electrocardio detecting contacts, and a body temperature detecting contact; the health analysis unit is provided by local or cloud service, and is linked with the health inspection and control unit in communication; the standing plate handrails are provided on the base; the angle adjusting standing plate is provided facing the handrails and at one side of the base; an upper surface of the angle adjusting standing plate is provided with a treading area, the angle of the angle adjusting standing plate is adjustable with one side edge as a baseline; the health analysis unit is used to analyze health information of a user collected by the health inspection and control unit, acquire a health analysis result of the user and provide a health solution, wherein a slide track being foldable on the base is provided between the base and the angle adjusting standing plate, and the angle adjusting standing plate rests on the slide track in a manner of being slidable back and forth.

2. The multi-angle electric exercise equipment of claim 1, wherein the angle adjusting standing plate comprises a seat, an outer case, and a lifting mechanism; the outer case covers over the seat; the lifting mechanism is provided inside the seat and the outer case; the upper surface of the outer case is provided with the treading area; the lifting mechanism enables the outer case to be adjusted in angle with one side edge as the baseline.

3. The multi-angle electric exercise equipment of claim 2, wherein the treading area is provided with an anti-slip mat therein.

4. The multi-angle electric exercise equipment of claim 1, wherein the treading area is provided with an anti-slip mat therein.

5. The multi-angle electric exercise equipment of claim 4, wherein the health inspection and control unit further comprises a music modulation module; the music modulation module is used to collect user's voice information, and acquire a basic frequency of a user voice, the central control module determines a voice basic frequency interval of the user according to the basic frequency of the voice, and selects and plays music matched with the voice basic frequency interval.

6. The multi-angle electric exercise instrument of claim 4, wherein the health inspection and control unit is further integrated with a power button, an earphone interface, an up button, and a down button; the power button is provided below the display module, and the up button and the down button are used to control the angle adjustment of the angle adjusting standing plate; the earphone interface is provided below the display module.

7. The multi-angle electric exercise instrument of claim 1, wherein the central control module is provided in a middle part of the handrails, and is electrically connected to the display module, the data processing module, and the wireless transmission module; the data processing module is electrically connected to the physical sign inspection module, for converting an analog signal detected by the physical sign inspection module to a digital signal; the display module is used to select a health inspection item and display health information and a health solution.

8. The multi-angle electric exercise equipment of claim 1, further comprising a power management unit and a power switch, the power management unit being used for power-off protection and charge/discharge management, and the power switch being provided on the base.

9. A control method for the multi-angle electric exercise equipment of claim 1, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

10. A control method for the multi-angle electric exercise equipment of claim 2, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

11. A control method for the multi-angle electric exercise equipment of claim 4, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

12. A control method for the multi-angle electric exercise equipment of claim 7, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

13. A control method for the multi-angle electric exercise equipment of claim 5, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

14. A control method for the multi-angle electric exercise equipment of claim 6, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;
   S3: processing the health information of the user, and acquiring the health analysis result of the user;
   S4: providing a corresponding modulation method and the exercise equipment according to physical condition information of the user.

15. A control method for the multi-angle electric exercise equipment of claim 8, comprising:
   S1: performing angle adjustment of the angle adjusting standing plate and selection of the health inspection item through the health inspection and control unit;
   S2: performing, by the angle adjusting standing plate, the angle adjustment of the angle adjusting standing plate as needed; after performing the selection of the health inspection item, collecting and monitoring health information of a user according to the selected health inspection item;

S3: processing the health information of the user, and acquiring the health analysis result of the user;

S4: providing a corresponding modulation method and the exercise equipment according to physical condition information of the user.

\* \* \* \* \*